United States Patent
Lebeau

[11] Patent Number: 5,129,009
[45] Date of Patent: Jul. 7, 1992

[54] METHOD FOR AUTOMATIC SEMICONDUCTOR WAFER INSPECTION

[75] Inventor: Christopher J. Lebeau, Tempe, Ariz.

[73] Assignee: Motorola, Inc., Schaumburg, Ill.

[21] Appl. No.: 533,207

[22] Filed: Jun. 4, 1990

[51] Int. Cl.[5] .............................................. G06K 9/00
[52] U.S. Cl. ..................................... 382/8; 358/101; 358/106; 382/22; 382/30
[58] Field of Search .................. 382/8, 32, 34, 41, 49, 382/22; 358/101, 106, 107, 388

[56] References Cited

U.S. PATENT DOCUMENTS

| | | | |
|---|---|---|---|
| 4,441,207 | 4/1984 | Loughheed et al. | 382/8 |
| 4,477,926 | 10/1984 | Linger et al. | 382/8 |
| 4,481,664 | 11/1984 | Linger et al. | 382/8 |
| 4,618,938 | 10/1986 | Sandland et al. | 358/106 |
| 4,648,052 | 3/1987 | Fridge | 382/8 |
| 4,659,220 | 4/1987 | Bronte et al. | 358/106 |
| 4,731,855 | 3/1988 | Suda et al. | 382/8 |
| 4,805,123 | 2/1989 | Specht et al. | 382/8 |
| 4,853,967 | 8/1989 | Mandeville | 358/106 |
| 4,893,346 | 11/1990 | Bishop | 382/8 |
| 4,965,842 | 10/1990 | Crossley et al. | 358/107 |

*Primary Examiner*—Joseph Mancuso
*Attorney, Agent, or Firm*—Joe E. Barbee; Stuart T. Langley

[57] ABSTRACT

An automatic integrated circuit inspection method is provided wherein an image of an integrated circuit is obtained and a direction edge enhancement is performed. An image of an integrated circuit under inspection is then obtained and the direction edge enhancement performed. The second edge enhanced image is then logically compared to the first edge enhanced image. Preferably, the first edge enhanced image is dilated while the second edge enhanced image is skeletonized to improve robustness of the system allowing for magnification and rotation errors in either the sample image or the image under inspection. Further, defects which are located are then classified by obtaining a plurality of images of the defect while changing light conditions. The plurality of defect images are combined to form a feature matrix which is then compared against an expert system database having a large number of feature matrices associated with defect classifications.

3 Claims, 5 Drawing Sheets

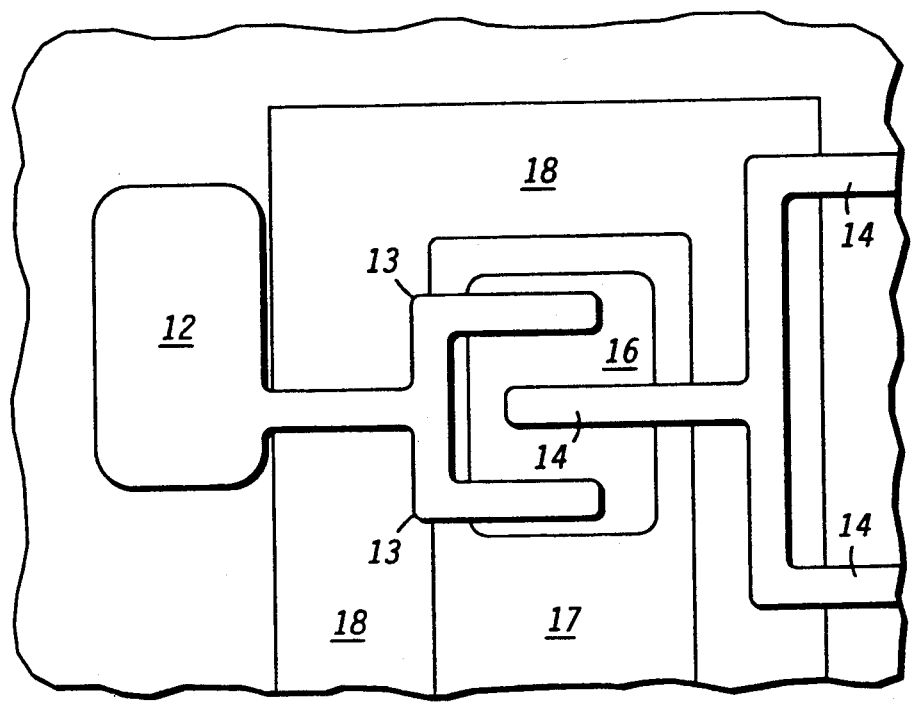
FIG. 1
FIG. 2
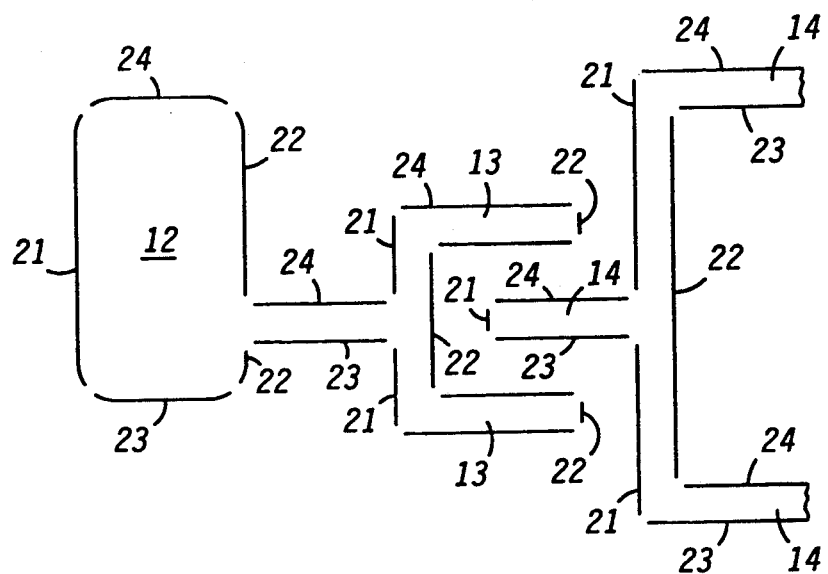

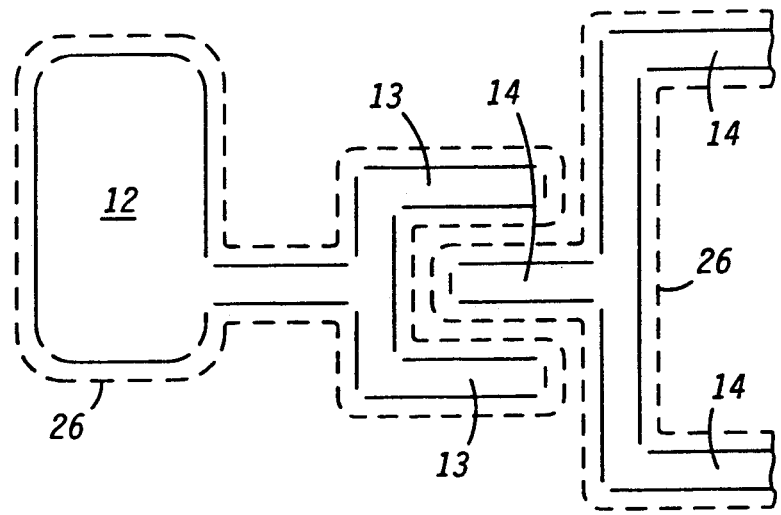
FIG. 3
FIG. 4
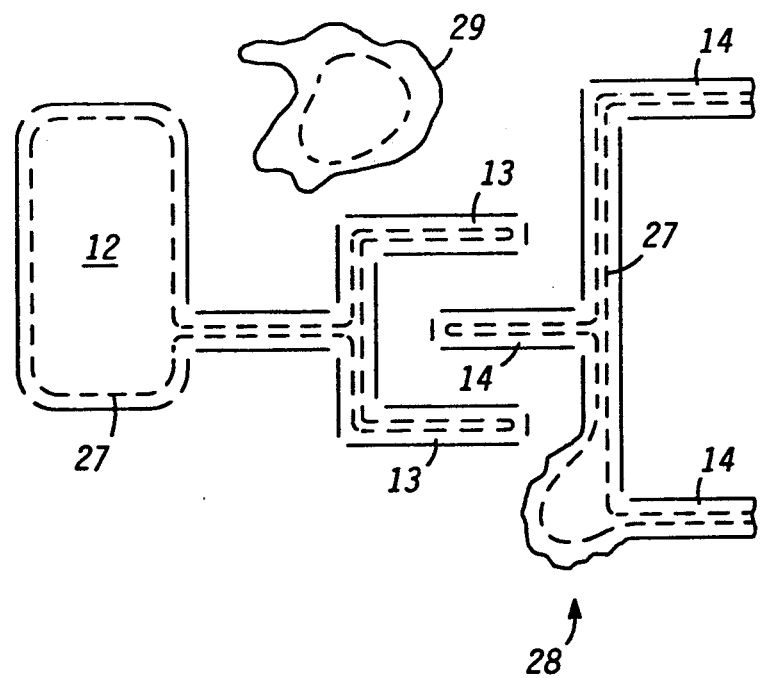

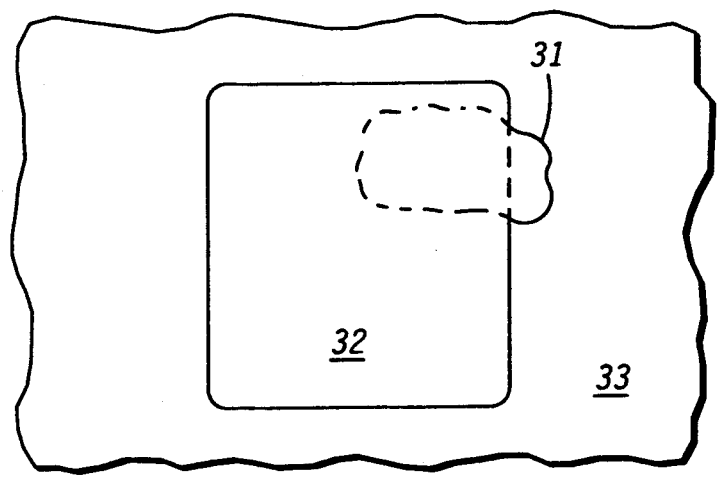
FIG. 6A
FIG. 6B
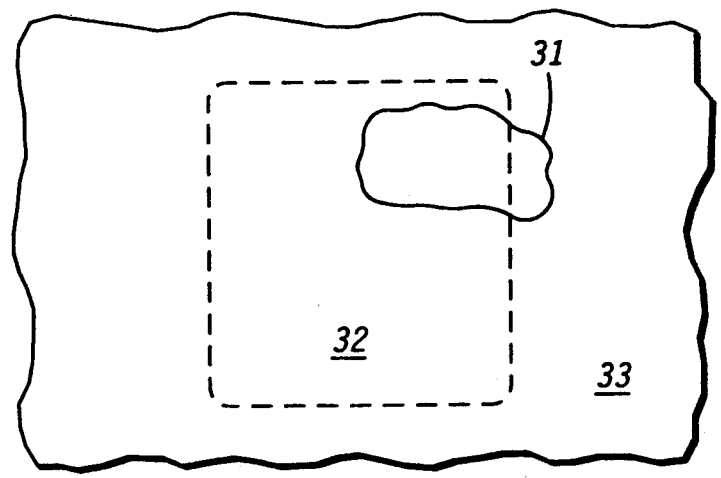

METHOD FOR AUTOMATIC SEMICONDUCTOR WAFER INSPECTION

BACKGROUND OF THE INVENTION

This invention relates in general to inspection of integrated circuit wafers, and more particularly, to a method for automatically inspecting a patterned wafer.

In view of the time consuming nature of manual inspection of semiconductor wafers, a great emphasis has been placed on automating all inspection operations. Recently, inspection of unpatterned starting wafers for cleanliness has been automated. Patterned wafers, however, continue to be inspected manually. Manual inspection usually involves microscopic inspection of a handful of sights on a semiconductor wafer using ordinary white light and less often using dark field microscopes. Manual inspection operations are performed several times during each photolithography step in addition to numerous inspections which occur after processing is complete.

Defect density is known to be a major yield limit in semiconductor manufacture and must be monitored to provide data for yield control. Accurate defect density measurements can also be used to predict reliability and lifetime of an integrated circuit. Unfortunately, due to the time consuming nature of manual inspection only a few circuits out of several hundred, or thousand, which are formed on a single wafer are ever inspected. Further, as the circuits become more complicated and patterns become smaller, it becomes increasingly difficult to see defects, let alone classify such defects. Present methods of integrated circuit inspection provide only estimates of defect density and thus can not fulfill the greater needs of the semiconductor industry.

Although manual inspection is rather simple and requires relatively low cost equipment, the results are somewhat inconsistent because of the subjective nature of the assessment and the attention span of the operator. Further, the time required to process the wafers as well as the limited amount of information that may be readily obtained limits the application of manual inspection techniques to statistical sampling. If such an inspection were to be carried out on all of the processed wafers, astronomical cost inefficiencies would result. In practice, this detection procedure is carried out on only a small percentage of the processed wafers. Such a procedure is grossly inefficient in that 90% or more of the processed circuits are never inspected.

Thus, a need has developed in the semiconductor industry to provide an automatic processed semiconductor wafer inspection system which can inspect all of the circuits of a large number of wafers in a time efficient manner and can classify defects which are found in the integrated circuits.

Accordingly, it is an object of the present invention to provide an improved time efficient integrated circuit inspection method.

Another object of the present invention is to provide an integrated circuit inspection system with a high immunity to variable light conditions such as lighting intensity, magnification, and rotation of the circuits under inspection.

A further object of the present invention is to provide an integrated circuit inspection system which can classify defects and anomalies on the surface of the integrated circuit.

Still another object of the present invention is to provide a method of inspecting pattered integrated circuits using direction edge enhanced images of the integrated circuit.

A further object of the present invention is to provide a method of inspecting semiconductor wafers and classifying defects thereon using a plurality of images of the defect obtained by varying light conditions.

SUMMARY OF THE INVENTION

These and other objects and advantages of the present invention are achieved by providing an automatic integrated circuit inspection system wherein an image of a first integrated circuit is obtained and a first direction edge enhancement is performed. An image of an integrated circuit under inspection is then obtained and the direction edge enhancement performed. The second edge enhanced image is then logically compared to the first edge enhanced image. Preferably, the first edge enhanced image is dilated while the second edge enhanced image is skeletonized to improve robustness of the system allowing for magnification and rotation errors in either the sample image or the image under inspection.

Defects which are located are then classified by obtaining a plurality of images of the defect while changing light conditions. For example, by exposing the defect to red, green, and blue light alternately and/or exposing the defect to light at varying angles of incidence, a variety of defect features such as texture, size, shape, location and the like can be identified. The plurality of defect images are analyzed to provide and together to form a feature matrix which is then compared against an expert system database having a large number of feature matrices associated with defect classifications.

BRIEF DESCRIPTION OF THE DRAWINGS

FIG. 1 illustrates a top view of a small portion of an integrated circuit which can be inspected using the method of the present invention;

FIG. 2 illustrates a direction edge enhanced image of a portion of the integrated circuit shown in FIG. 1;

FIG. 3 illustrates a morphologically dilated image of a sample integrated circuit; and FIG. 4 illustrates a skeletonized image of an integrated circuit under inspection;]

FIG. 6A-B illustrate operation of the defect classification system of the present invention.

DETAILED DESCRIPTION OF THE DRAWINGS

Figure 5A:
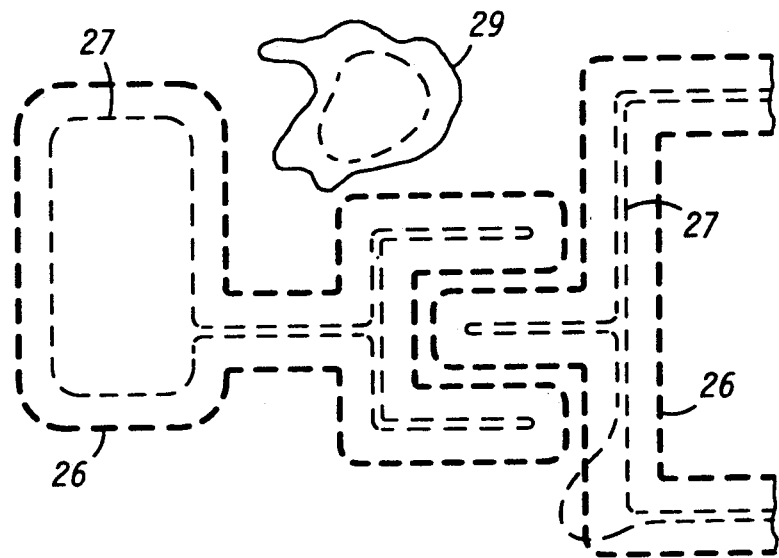
FIGS. 5A-B illustrate comparisons between skeletonized images and dilated images.

FIG. 1 illustrates a highly magnified view of a portion of an integrated circuit 11. Although a relatively simple bipolar integrated circuit is shown for ease of description, it should be understood that the method of the present invention is equally applicable to very complex integrated circuits having thousands or millions of components and is applicable to CMOS, bipolar, or any similar integrated circuit manufacturing technology.

Integrated circuit 11 comprises an isolation region 18 in which is formed a collector region 17. Base region 16 is formed in collector region 17 and emitter region (not shown) is formed near the central portion of base region 16 under emitter electrode 14. Base region 16 is contacted by base fingers 13 which are coupled to bonding pad 12. Bonding pad 12, base fingers 13, and emitter interconnect 14 are formed of metal, while base 16, collector 17, and isolation region 18 are covered by oxides of various thicknesses. Because oxide over various portions of integrated circuit 11 have different thicknesses, each region appears to have a different color when exposed to white light. Usually, the emitter, base, collector, and isolation regions, as well as device regions, are easily discernible under white light, although occasionally it may be necessary to filter the light to increase definition between regions.

One difficulty with conventional inspection systems is that the actual color of each of the regions may vary significantly from wafer to wafer or even from device to device on a single wafer. While each of the regions remains easily discernible to the naked eye, this change in absolute color often confuses an image processing system. This confusion leads to judgment errors in identifying good and bad device structures and leads to an increased amount of operator intervention to fine tune optics or manually inspect portions of a wafer. A particular advantage of the present invention is its ability to accurately inspect the surface of an integrated circuit with even widely varying colors across a single wafer. It is this aspect of the present invention which is referred to as "robustness".

FIG. 2 illustrates a direction edge enhanced image of bonding pad 12, base fingers 13, and emitter electrode 14. FIG. 2 shows the metallization pattern which is shown in FIG. 1 including bonding pad 12, base fingers 13, and emitter interconnect 14. Base 16, collector 17, and isolation region 18 have been omitted from FIG. 2 for ease of illustration, but it should be understood that the alignment and quality of these regions can be inspected simultaneously with the metallization pattern shown in FIG. 2. It should also be understood that by varying light conditions and/or intelligently varying the threshold conditions of the image analysis system, that specific areas or layers of integrated circuit 11 can be analyzed while ignoring other layers. This feature will become more apparent during the discussion of defect classification which follows.

Although physical breaks are shown between edges of the image to aid understanding, it should be understood that these breaks may or may not occur. A direction edge enhanced image identifies edges of interest in the pattern shown in FIG. 1 using any of a number of well known image analysis algorithms. The direction edge enhanced image includes east edges 21, West edges 22, South edges 23, and North edges 24. The direction edges combine to form a direction edge shape which is merely a shape contained by a series of connecting direction edges. Direction edge enhancement affords many advantages in image processing including reduced quantity of data, greater flexibility of data, and immunity to such variations as illumination intensity and color variation in the image. For the purpose of integrated circuit inspection, the direction edge enhanced image contains all information of interest in inspection while using a fraction of the data which would be required using a pure gray scale analysis technology.

The method of the present invention compares direction edge images of two similar integrated circuits to identify anomalies or defects in one of the integrated circuits. The two integrated circuits may be adjacent to each other or located in different areas of the wafer, or indeed located on entirely different wafers. It is useful, however, if the integrated circuits are adjacent to each other as this greatly eases compensation for color variation and pattern magnification which occurs during normal semiconductor processing.

In the method of the present invention first image, or sample image, is obtained and analyzed. The analysis includes a direction edge enhancement of the sample image as shown in FIG. 2, and preferably includes a morphological dilation, as shown in FIG. 3. Morphological dilation of the direction edge shape is nothing more than a mathematical transformation of the direction edge shape which has the effect of growing the direction edge shape's boundary by one or more picture elements or pixels. This results in a swelled, or dilated direction edge image illustrated by dashed line 26 in FIG. 3. Dilated direction edge shapes of the sample integrated circuit are stored for future comparison.

FIG. 4 illustrates a direction edge shape of an integrated circuit under inspection which will be compared to the dilated direction edge shape 26 shown in FIG. 3. The direction edges in FIG. 4 and FIG. 3 are not individually labeled as they were in FIG. 2 but it should be understood both FIG. 4 and FIG. 3 illustrate in solid lines the same direction edge enhanced image shown in FIG. 2. In the method of the present invention the direction edge shape of the integrated circuit under inspection is skeletonized or eroded to produce a skeletonized direction edge shape illustrated by dashed lines 27. The skeletonizd process is another mathematical transformation opposite the dilation process in that direction edge shapes are shrunk by one or more picture elements. Mask flaw 28 and debris 29 also produce direction edge shapes which are skeletonized. The skeletonization process reduces the overall size of the direction edge shape while maintaining critical information such as overall shape and position. The dilation process illustrated in FIG. 3 and the skeletonization process shown in FIG. 4 are optional but greatly improve the robustness of the image analysis system.

Skeletonized shape 27 is subsequently compared to dilated shape 26 as shown in FIG. 5A. This comparison is performed by logically comparing points which make up skeletonized image 27 to determine if they fit within the boundaries defined by dilated image 26. Those points which do not fit within the boundaries of dilated image 26 indicate anomalies or defects in the pattern. The location for each anomaly or defect is determined and recorded. Additionally, further information such as size and shape of each defect can be recorded. Further analysis and classification of defects 29 and 28 will be described hereinafter in reference to FIG. 6. The logical comparison step can be performed by a system computer which is coupled to image analysis computer.

Figure 5B:
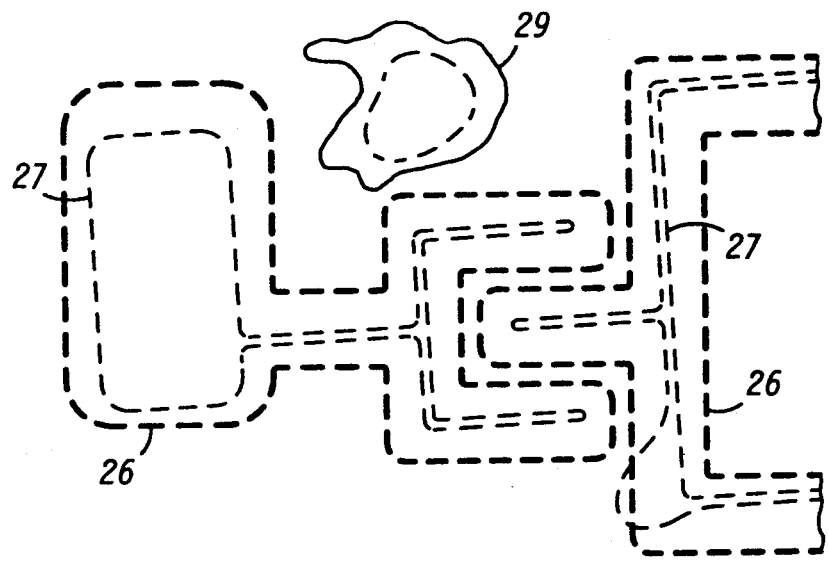

FIG. 5B illustrates the advantage of the dilation and skeletonization processes. In FIG. 5B skeletonized image 27 is rotted somewhat with respect to dilated image 26. Acceptable image variations include rotation, as shown in FIG. 5B, as well as absolute location variation, also called x or y shift, and magnification variation. Such image variations can easily occur in a manufacturing environment due to either misregistration of a wafer under inspection or shifting of the optics which make up the inspection system. It can be seen however that skeletonized image 27 still remains within the boundaries of dilated image 26 except for flaw 28 and defect 29. Thus, even when normal errors occur in the inspection equipment a correct analysis of the integrated circuit is provided.

It should be apparent that analysis of the sample integrated circuit and analysis of the integrated circuit under inspection can be performed sequentially or in parallel depending on the equipment setup. For example, parallel inspection would require two sets of optics to view the sample integrated circuit and the integrated circuit under inspection simultaneously. To perform the operation sequentially the direction edge image or dilated direction edge image 26 shown in FIG. 2 must be stored while the image of the integrated circuit under inspection is analyzed. Since the logical comparison between the two images is performed digitally by a computer either parallel inspection or sequential inspection and comparison are acceptable applications of the present invention. Particular choice of operation will be decided by capital expenditure and operating speed demands.

As indicated earlier, it is preferable to compare adjacent integrated circuits while indexing across a wafer. This means that for each inspection, a new sample chip is used, and that once an IC has been inspected, it becomes the sample IC for inspection of the adjacent IC. This process is continued until an entire wafer has been inspected. Of course, only a few chips on a wafer may be inspected, if desired, using the comparison method of the present invention.

Once defects 29 and 28 are identified it is very useful to automatically classify these defects. This classification provides useful information for process control and reliability prediction. Basic information such as defect location, size, and shape can be obtained directly by mathematical analysis of the direction edge shape which has been identified as a defect. More detailed analysis can be provided by obtaining a plurality of images of each defect under a variety of lighting conditions. For example, each defect can be illuminated with red, blue, and green light and/or can be illuminated with light at varying angles of incidence.

FIG. 6A and 6B illustrate a defect which is illuminated under two different light conditions. Both FIG. 6A and 6B show a highly magnified portion of integrated circuit 11 with a defect 31 which occurs over an active region 32. FIGS. 6A and 6B show direction edge images obtained by the image analysis system under differing light conditions. Background region 33 may be another active device region or an inactive portion of integrated circuit 11. Direction edges, which are derived from the image, are shown in solid lines, while dashed lines indicate portions of the actual image which are not represented by direction edges under a particular lighting condition.

Direction edges of an image are identified by locating portions of the image where reflected light intensity changes. If two portions of the image reflect nearly the same light intensity, edge information is difficult to discern as the two portions of the image appear to be one continuous portion. Usually, direction edge analysis is performed under broad spectrum lighting to maximize the difference in reflected light intensity. The present invention, on the other hand, uses predetermined lighting conditions to selectively enhance and diminish edge features.

Information shown by the dashed lines in FIG. 6A and FIG. 6B is lost under a particular lighting condition because reflected light intensity between defect 31 and active region 32 is not sufficiently different to be detected. For example, under white light or broad spectrum illumination, defect 31 may appear orange, active area 32 may appear red, and background 33 may appear green. These colors, of course, are chosen for descriptive purposes only, and may vary significantly in actual devices. Under red light illumination, however, the color difference between orange defect 31 and red active area 32 is too slight to be detected. Thus, edges which are apparent under white light are not discernable under red light. Under this particular lighting condition a direction edge image containing only the information shown in solid lines in FIG. 6A is obtained. The set of direction edge information shown in solid lines in FIG. 6A thus forms a first feature vector containing information about the defect and the integrated circuit under the first lighting condition.

FIG. 6B shows the same integrated circuit under a different lighting condition in which the difference between active area 32 and background 33 is not discernable, but defect 31 is discernable. The set of direction edge data shown by solid lines in FIG. 6B forms a second feature vector describing the defect and surrounding integrated circuit. It should be noted that the direction edge information contained in each of the feature vectors is unique to the lighting condition.

Any number of lighting angles and lighting colors can be used to provide additional feature vectors although lighting with the primary colors red, green, and blue combined with just a few incident light angles is believed to provide enough information to correctly classify most defects. The plurality of feature vectors are combined to form a feature matrix describing the defect. This feature matrix is then fed into an expert system database which compiles information on feature matrices and associates feature matrices with defect classifications. As this database builds up it can be used to classify defects without assistance from an expert.

Figure 7:
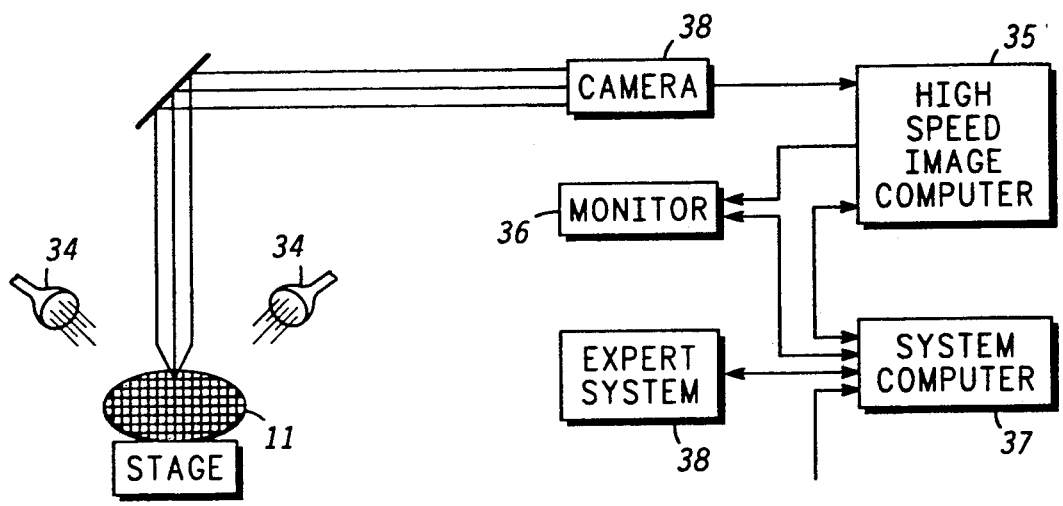
FIG. 7 illustrates, in block diagram form, an integrated circuit inspection system of the present invention.

A block diagram of the expert system defect classification of the present invention is shown in FIG. 7. Integrated circuits 11 are illuminated by a variety of light sources 34 which are described hereinbefore. An industrial television camera 38 detects the image from integrated circuits 11 and feeds the image information to a high speed image computer 35. High speed image computer 35 is particularly adapted for processing both binary and gray level images and performing such functions as direction edge enhancement, morphological dilation, and morphological skeletonization. This processed image is then sent to a monitor on which an operator can visually observe the inspection process. High speed image computer 35 is also coupled to a system computer 37 which performs such functions as determining a location size and shape of various features and defects on integrated circuit 11. System computer 37 also compiles feature vectors and build feature matrices during defect classification process. Feature matrices are then fed to expert system 38 which classified the defects and stores the feature matrices with the defect classification for future reference.

By now it should be appreciated that an improved, robust integrated circuit inspection method has been provided. By using direction edge enhanced images and techniques such as skeletonization and dilation of these images, robustness of the system is greatly improved and therefore the system can be highly automated. Defect locations can be easily identified and stored on a real time basis for all of the integrated circuits on a wafer. Further, defects which are located can be analyzed using a variety of lighting sources to obtain a plurality of defect images which are converted to feature vectors. Feature vectors are combined to build feature matrices which are then unique identifiers which can be used to classify the defects providing valuable information for process control and circuit reliability.

I claim:

1. A method of inspecting a semiconductor integrated circuit (IC) comprising: obtaining an image of the IC; performing direction edge enhancement of the image to form a direction edge shape; skeletonizing the direction edge shape; testing the skeletonized direction edge shape for correlation to a predetermined shape which has been previously stored; identifying an anomalous shape which cannot be correlated to the stored predetermined direction edge shape and classifying the anomalous shape wherein the step of classifying the anomalous shape further comprises: obtaining a plurality of images of the anomaly under varied lighting angles and lighting colors; building a feature matrix using the plurality of images; and comparing the feature matrix to an expert data base having feature data associated with defect classification data.

2. A method for automatically inspecting a patterned integrated circuit (IC) comprising:

analyzing a first IC including the steps of obtaining an image of a pattern formed on a first IC; deriving a first direction edge image from the image of the first IC's pattern;

analyzing a second IC including the steps of obtaining an image of another pattern formed on a second IC; deriving a second direction edge image from the image of the second IC's pattern; and logically comparing the second direction edge image to the first direction edge image to identify anomalies in the second IC's pattern which do not correspond to the first IC's pattern; storing a location of each anomaly identified after the logical comparison step; illuminating an identified anomaly with a variety of colors of light; obtaining a number of color images of the anomaly under each color of illumination; storing each of the color images;

illuminating the anomaly at a variety of incident light angles; obtaining a number of on/off axis images of the anomaly at each incident light angle; storing each of the on/off axis images;

building a feature vector for the anomaly; building a feature matrix for the anomaly; providing a data base having defect classification associated with anomaly feature information; and comparing the feature vector and feature matrix to the data base to classify the anomaly.

3. The method of claim 2 further comprising manually determining a defect classification for the anomaly and storing the features matrix data in the data base along with its associated defect classification.

* * * * *